United States Patent [19]

Gersten et al.

[11] Patent Number: 4,459,356

[45] Date of Patent: Jul. 10, 1984

[54] RADIOACTIVE STAINING OF GELS TO IDENTIFY PROTEINS

[75] Inventors: Douglas M. Gersten, Washington, D.C.; Edward J. Zapolski, Arlington, Va.; Robert S. Ledley, Silver Spring, Md.

[73] Assignee: Georgetown University, Washington, D.C.

[21] Appl. No.: 348,075

[22] Filed: Feb. 11, 1982

[51] Int. Cl.$^3$ .............................................. C09K 11/04
[52] U.S. Cl. ..................................................... 436/86
[58] Field of Search ........................ 424/1, 1.5, 2, 3, 7, 424/1.1; 23/230 B, 919; 252/408, 301.1; 260/429.1; 250/303; 546/10; 436/86, 63, 174; 204/180 G

[56] References Cited

U.S. PATENT DOCUMENTS

| | | | |
|---|---|---|---|
| 3,673,410 | 6/1972 | Waite et al. | 250/106 T |
| 3,678,148 | 7/1972 | Caiola | 424/1 |
| 3,773,467 | 11/1973 | Yang et al. | 23/230 B |
| 3,801,783 | 4/1974 | Caiola | 250/303 |
| 3,856,930 | 12/1974 | Nodine et al. | 424/1 |
| 3,887,332 | 6/1975 | Takase et al. | 23/230 B |
| 3,925,020 | 12/1975 | Ogawa et al. | 23/230 B |
| 3,959,455 | 5/1976 | Ansari et al. | 424/1 |
| 4,129,644 | 12/1978 | Kalopissis et al. | 424/59 |
| 4,219,337 | 8/1980 | Grossberg et al. | 23/230 B |
| 4,256,727 | 3/1981 | Triplett et al. | 424/1.5 |

OTHER PUBLICATIONS

Kobodera, A. et al., Radioisotopes, vol. 23, pp. 628-634 (1974).
Zapolski, E. J. et al., Analytical Biochemistry, vol. 123, pp. 325-328.
Merril et al., "Ultrasensitive Stain for Proteins in Polyacrylamide Gels Shows . . . ", *Science*, vol. 211 (3/27/81), pp. 1437-1438.
O'Farrell, "High Resolution Two-Dimensional Electrophoresis of Proteins," *J. Biol. Chem.*, vol. 250 (5/27/75), pp. 4007-4021.
Elder et al., "Radioiodination of Proteins in Single Polyacrylamide Gel Slices," *J. Biol. Chem.*, vol. 252 (9/25/77), pp. 6510-6515.
Graham et al., "Polyacrylamide Gel Staining with Fe$^{2+}$-Bathophenanthroline Sulfonate," *Anal. Biochem.*, vol. 88 (1978), pp. 434-441.
Poehling et al., "Visualization of Proteins with a Silver 'Stain': A Critical Analys," *Electrophoresis*, vol. 2 (1981), pp. 141-147.
Laemmli, U. K., "Cleavage of Structural Proteins During the Assembly . . . ", *Nature*, vol. 227 (8/15/70), pp. 680-681.
Sammons et al., "Ultrasensitive Silver-Based Color Staining of Polypeptides in . . . ", *Electrophoresis, vol. 2 (1981), pp. 135-141.*

*Primary Examiner*—Brooks H. Hunt
*Assistant Examiner*—M. Moskowitz
*Attorney, Agent, or Firm*—Oblon, Fisher, Spivak, McClelland & Maier

[57] ABSTRACT

Radioactive staining of gels is employed to identify proteins. A radioactive stain composition is formed by introducing radioactive iron isotope into ferrous bathophenanthroline sulfonate by adding crystalline ascorbic acid and acetic acid to a $^{59}$FeCl$_3$ solution, adding aqueous BPS solution after the dissolution of the crystals, and adding methanol and acetic acid to yield the radioactive stain composition. Alternatively, the radioactive stain composition may be formed by bombarding a non-radioactive stain with thermal neutrons. The method of identifying proteins with the radioactive stain composition basically comprises the steps of placing the protein in the gel, forming a radioactic stain composition, and applying the radioactivated stain composition to the gel. To demonstrate the protein present, either a gamma scintillation counting technique or radioautography is preferably employed.

17 Claims, 4 Drawing Figures

ROD GEL

SLAB GEL ially, the present invention relates to radioactive staining of gels to identify proteins.

RADIOACTIVE STAINING OF GELS TO IDENTIFY PROTEINS

BACKGROUND OF THE INVENTION

1. Field of the Invention

The present invention generally relates to radioactive staining of gels to identify proteins. More specifically, the invention relates to the preparation of a radioactive stain composition, and to the utilization of the radioactive stain composition in an overall method of identifying proteins.

2. Description of the Prior Art

The arsenal of stains available for the detection of polypeptides in polyacrylamide gels after separation by electrophoresis is already quite extensive but there is always a quest for more sensitive reagents. The enhancement of detection that is afforded by recently developed techniques, such as the silver stain technique, not only compensates for the diminished protein load in methods employing very thin gels but can also reveal polypeptide components that are undetected by conventional Coomassie Blue stain. See article by C. R. Merril, D. Goldman, S. A. Sedman, and M. H. Ebert in *Science*, vol. 211, pp. 1437-1438 (1981).

One of the most powerful visualization tools, radioautography, is presently limited to experiments which are conducted with intrinsically labelled proteins produced from substrates containing radioactive labelled amino acids. See article by P. H. O'Farrell, in *J. Biol. Chem.*, vol. 250, pp. 4007-4021 (1975). Moreover, extrinsic radioactive labelling techniques, such as iodination, can alter the electrophoresis properties of proteins, and the isotope is not necessarily uniformly linked to each protein and non-selectively distributed among all polypeptide components of the mixture.

Direct iodination of separated proteins in polyacrylamide gels has been reported by Edler et al (see the article by J. H. Edler, R. A. Peckett II, J. Hampton, and R. A. Lerner in the *J. Biol. Chem.*, vol. 252, pp. 6510-6515 (1977)). This technique is quite useful when used to study radioactive peptides after tryptic digestion, but it has been found that some lots of acrylamide contain a contaminant which also becomes radioiodinated, and this negates its utility for radioautography.

It has been reported that ferrous bathophenanthroline sulfonate (BPS) is well suited for protein staining because of its reproducability. When so utilized, it rapidly stains and destains, yielding clear backgrounds and reproducable results. See the article by G. Graham, R. S. Nairn and G. W. Bates in *Anal. Biochem.*, vol. 88, pp. 434-441 (1978).

However, such prior art techniques are burdened by certain disadvantages. For example, such techniques are often quite complex and slow. In addition, such prior art techniques often involve modifications of the proteins prior to electrophoresis.

Furthermore, in prior art techniques involving radioiodination of proteins, the radioiodination procedure may be hazardous to the user. In those techniques involving prior labelling, such prior labelling requires individual treatment (experimentation) for each sample. In addition, the prior art techniques, by virtue of their complexity and slowness, are necessarily quite costly.

Finally, prior art techniques are typically not sensitive to low-level protein presence; that is, such techniques are not as sensitive as they should be, and accordingly cannot demonstrate low protein levels. In the techniques of the prior art, such as those involving sensitive stains such as silver, such sensitive stains do not stain all proteins with equal efficiency; accordingly, a non-uniformity in staining results.

SUMMARY OF THE INVENTION

Therefore, the present invention relates to radioactive staining of proteins in gels to identify the proteins. More specifically, the invention relates to the development of a radioactive stain compensation, including the process of preparing such radioactive stain composition, as well as the utilization of the radioactive stain to identify proteins in an overall method of identifying proteins.

As such, the present invention has certain advantages over the prior art techniques discussed above. For example, the inventive radioactive stain labelling technique, when employed as a part of a method of identifying proteins, is simple and rapid relative to prior art techniques. Moreover, it does not involve any modifications of the proteins prior to electrophoresis. The simplicity of preparing the radioactive composition, as well as the simplicity in the use of the simple staining and destaining procedures, provide a ready means for utilizing the powerful detecting capabilities of radioautography without resorting to modification of the proteins prior to electrophoresis. Thus, the present invention obviates some of the objections which have been raised to sensitive silver staining technique (see the article by H. M. Poehling and V. Neuhoff, in *Electrophoresis*, vol. 2, pp. 141-147 (1981)).

Therefore, it is an object of the present invention to provide a radioactive stain composition.

It is an additional object of the present invention to provide a process of preparing a radioactive stain composition.

It is an additional object of the present invention to provide a method of identifying proteins utilizing a radioactive stain composition to label the proteins.

It is an additional object of the present invention to provide a process of preparing radioactive stain composition, which process is simple and rapid.

It is an additional object of the present invention to provide a method of identifying proteins with radioactive stain composition, which method is simple and rapid.

It is an additional object of the present invention to provide a method of identifying proteins with radioactive stain composition, which method does not involve modifications of the proteins prior to electrophoresis.

The above and other objects that will hereinafter appear, and the nature of the invention, will be more clearly understood by reference to the following description, the appended claims, and the accompanying drawings.

DETAILED DESCRIPTION

Figure 1:
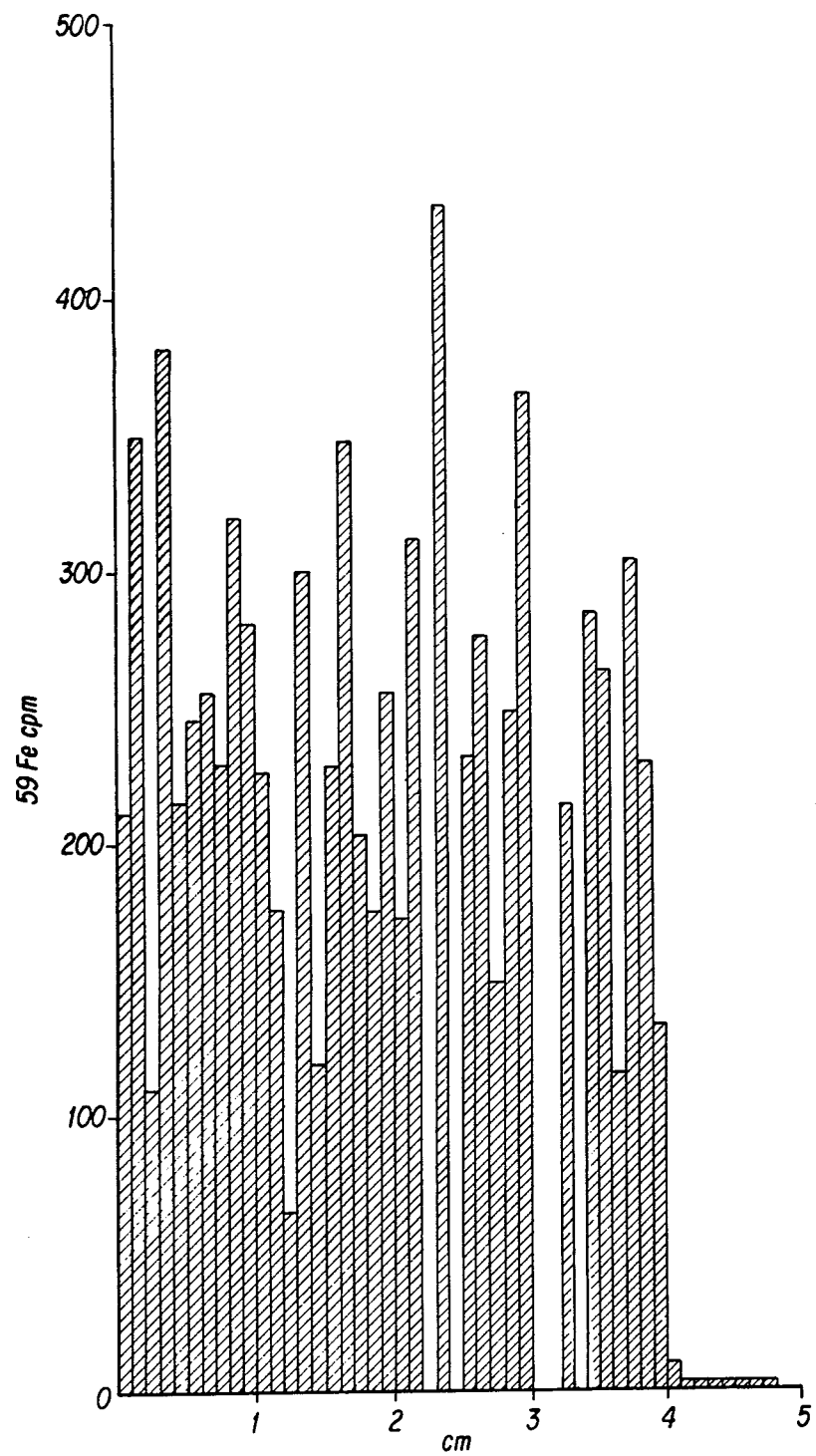
FIG. 1 illustrates the results obtained with an 0.1 microgram load of bovine serum albumin (BSA), in accordance with the first embodiment of the present invention.

The invention of the present application will now be more fully described with reference to the various figures of the drawings.

In accordance with the present invention, a radioactive stain composition is developed as a result of introduction of a radionuclide (e.g., radioactive iron isotope $^{59}Fe$, which is a strong gamma emitter having peaks of 1.1 and 1.3 MeV) into BPS to form ferrous BPS. It has been determined that introduction of such a radioactive iron isotope into the ferrous BPS molecule provides an ideal reagent for extrinsic radioactive labelling of proteins separated by polyacrylamide gel electrophoresis, and simple common staining-destaining procedures can be utilized. Such labelled gels are then used to detect submicrogram quantities of proteins either by radioautography or by excission of the gel and counting.

In order to prepare the radioactive stain composition, sodium bathophenanthroline sulfonate (BPS), ascorbic acid and Tris buffer salts were obtained from Sigma Chemical Co. (St. Louis, MO). Enzymes grade acrylamide, N,N' methylenebisacrylamide and N,N,N',N'-tetramethylethylenediamine (TEMED) are products of and were obtained from Eastman Kodak Co. (Rochester, N.Y.). Sodium dodecylsulfate (SDS) was obtained from Pierce Chemicals (Rockford, Ill.). The radioactive isotope ($^{59}FeCl_3$ in 0.05M HCl, specific activity 15.6 mC/mg) was purchased from New England Nuclear (Boston, Mass.), but was diluted to 10 ml with 0.5N HCl to yield an approximately 0.1 mM Fe(III) solution.

Bovine serum albumin and molecular weight standard markers were obtained from Sigma Chemical Co. and Pharmacia (Piscataway, N.J.), respectively. All other chemicals were reagent grade or better, and were used without further purification.

The $^{59}Fe$ BPS staining solution can be prepared in the following manner. To 0.8 ml $^{59}FeCl_3$ solution, 5 mg crystalline ascorbic acid and 5 ml of 10% (v/v) acetic acid were added to form a ferrous solution (from the latter, it is clear that at this point, one could begin with a ferrous starting solution or reductants other than ascorbic acid). After dissolution of the crystals, 0.3 ml of 0.001M aqueous BPS solution was added, and a noticeable pink ferrous BPS solution was formed. After waiting 5 minutes, 40 ml methanol and 45 ml 10% acetic acid were added to yield an approximate 0.001 mM $^{59}Fe(II)BPS$ reagent in 4:4:1 (methanol:water:acetic acid) staining solution. It should be noted that other radionuclides, such as $S^{35}$ and $Co^{60}$, could be used.

Staining to obtain identification of proteins within a gel was accomplished as follows. Initially, the protein was placed in the gel in a conventional manner. Then, the radioactive stain was prepared in the manner just described above. Finally, the stain was applied to the gel in a conventional manner, for example, in the manner set forth in the above-referenced article by Graham et al.

In an alternative embodiment of the method of the present invention, the protein is placed in the gel, and one or more of the following stains are chosen: Coomassie Blue (R), Coomassie Blue (G), Ponceau (S), Light Green (SF), Fast Green (SCF), and Amido Black (10B). One or more of these stains are then radioactivated by bombardment with thermal neutrons so as to form a radioactive stain composition. This is due to the fact that the stains contain radioactive sulfur $S^{35}$ (a beta emitter) when radioactivated. The radioactive stain composition is then applied to the gel in the same manner as with conventional stains, and the proteins to which the stains bind can be demonstrated by radioautography (as opposed to conventional color visibility techniques). In this manner, a lower level of protein can be detected, such lower level detection being achieved in contrast to prior art (color visibility) techniques.

Applicability of the proposed in situ radioactive staining technique was determined by staining protein samples in accordance with the first embodiment described above after electrophoresis in Laemmli-type gel rods (10 cm, 2.5 mm dia, 7.5% acrylamide and 0.1% SDS with 1 cm 3% stacking gel). See the article by U. K. Laemmli in *Nature*, vol. 227, pp. 680–681 (1970). The gels were fixed, stained and destained at 65° following the procedures described in the above-referenced article by Graham et at. The separating gel was sliced into mm segments, placed into test tubes, and counted in a well-type gamma scintillation counting system (radioautography could also be used).

FIG. 1 illustrates the results obtained with an 0.1 microgram load of bovine serum albumin (BSA). The histogram represents net cpm/mm gel from the beginning of the separating gel. Of the total $^{59}Fe$ activity, 84% was associated with a peak corresponding to BSA and 15% with a larger protein which may represent contaminant or BSA dimer.

Figure 2:
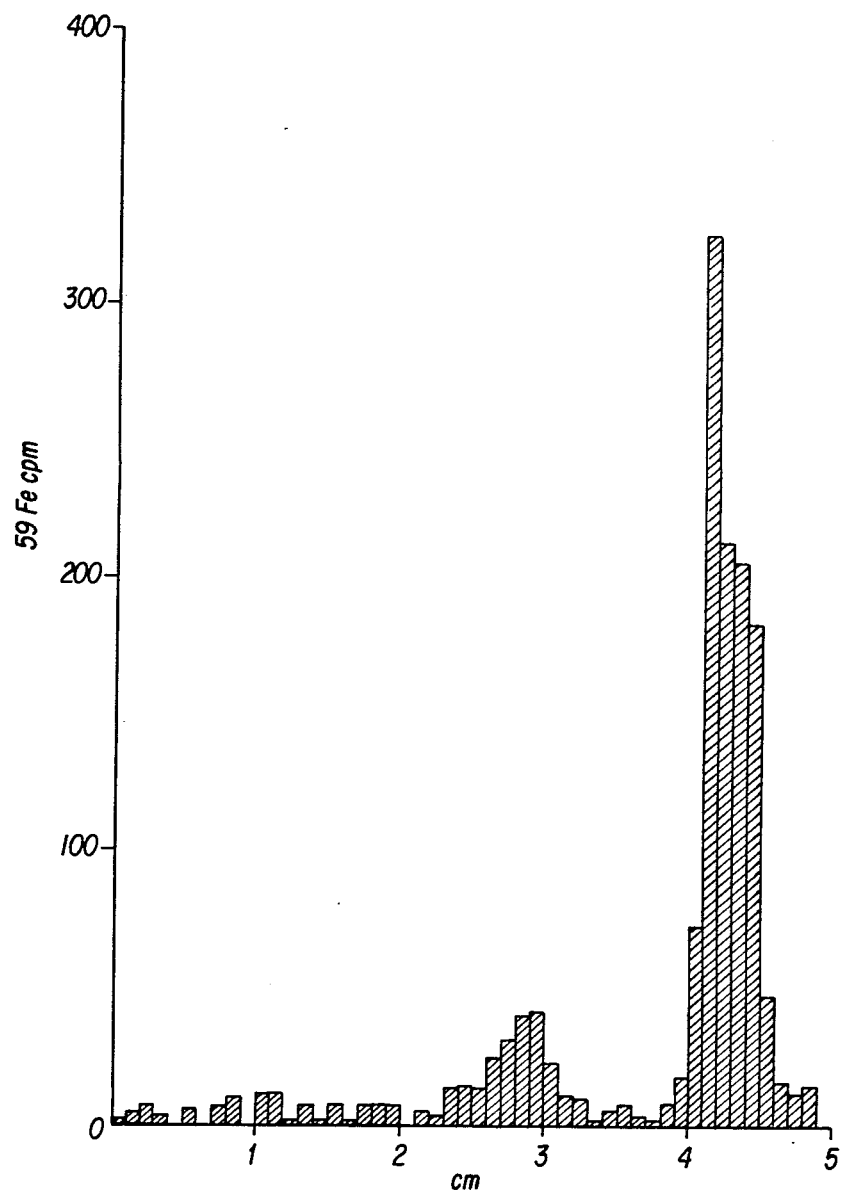
FIG. 2 illustrates the results obtained with an 0.1 microgram load of marker proteins, where at least nine distinct peaks of radioactivity are observed, in accordance with the first embodiment of the present invention.

FIG. 2 illustrates the results obtained with an 0.1 microgram load of marker proteins, where at least nine distinct peaks of radioactivity were observed. The procedure could also be applied to "counterstain", and thus label by radioactivity, gels that were previously fixed and stained with Coomassie Blue.

Applicability of the inventive radioactive staining technique was also determined by staining protein samples in accodance with the second embodiment described above, utilizing Laemmli-type gel slabs, and the proteins were demonstrated by radioautography (beta scintillation counting could also be used, but is not as efficient).

Figure 3A:
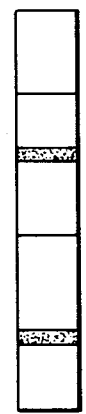
FIGS. 3A and 3B illustrate the demonstration of protein on a gel rod and gel slab, respectively, utilizing the radioactive staining technique of the second embodiment of the present invention.
Figure 3B:
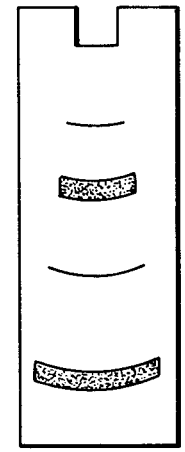

FIGS. 3A and 3B depict the demonstration of protein resulting from radiographic display of proteins as a result of employment of the second embodiment of the invention.

In summarizing the advantages of the present invention, radioactive stain labelling technique with $^{59}Fe$-ferrous BPS is simple and rapid. It does not involve any modifications of proteins prior to electrophoresis. Although the precise nature of the interaction of the reagent with denatured protein is not known, the reagent stains serum proteins to the same extent as Coomassie Blue, and does not exhibit selectiveness as to any of the individual proteins comprising the serum. The simplicity of the reagent's preparation, and the use of simple staining and destaining procedures, provide a ready means to utilize the powerful detecting capabilities of radioautography without resorting to modification of proteins prior to electrophoresis. This novel procedure may obviate some of the objections which have been raised with respect to the sensitive silver staining technique. See the article by H. M. Poehling and V. Neuhoff in *Electrophoresis*, vol. 2, pp. 141–147 (1981).

An additional advantage of the present invention resides in the fact that, in contrast to radioiodination techniques, the present invention involves no hazard to the user. In addition, whereas prior art techniques required prior labelling, which in turn required individual treatment (experimentation) for each sample, staining with radioactive stain in accordance with the present invention results in the advantage that the same baths can be used for several samples. In addition, since the method of the present invention is quite rapid and not complex, it is considerably cheaper than the prior art techniques. Moreover, the method is potentially more sensitive (that is, it can demonstrate lower levels of protein which are not able to be demonstrated by prior art techniques). Moreover, the present invention achieves uniformity in staining all proteins, in contrast to other sensitive stains (for example, silver) which do not stain all proteins with equal efficiency.

While preferred embodiments have been shown in illustrating the invention, it is to be clearly understood that various changes in detail and arrangement may be made without departing from the spirit and scope of this disclosure.

What is claimed is:

1. A radioactive stain composition comprising bathophenanthroline sulfonate and $^{59}$Fe radionuclide.

2. A process for the preparation of a radioactive stain composition, comprising the steps of:
   (a) adding a $^{59}$FeCl$_3$ solution to crystalline ascorbic acid and acetic acid to form an intermediate radioactive composition; and
   (b) adding the intermediate radioactive composition to aqueous bathophenanthroline sulfonate thereby forming said radioactive stain composition.

3. The process of claim 2, wherein 0.8 ml $^{59}$FeCl$_3$ solution is utilized.

4. The process of claim 2, wherein 5 mg crystalline ascorbic acid is utilized.

5. The process of claim 2, further comprising step (c) of adding methanol and acetic acid, wherein 5 ml of 10% (volume/volume) acetic acid is utilized.

6. The process of claim 2, wherein step (b) is implemented only after dissolution of the crystals contained in the crystalline ascorbic acid.

7. The process of claim 2, wherein step (b) results in the formation of a noticeable pink solution, and step (c) is not implemented until after a waiting period of substantially 5 minutes after formation of the noticeable pink solution.

8. A radioactive stain composition formed by the process of any one of claims 2, 3, 4 or 5.

9. A radioactive stain composition comprising a stain composition and a radionuclide selected from the group consisting of $^{59}$Fe, $^{35}$S and $^{60}$Co.

10. A process for the preparation of a radioactive stain composition which comprises bombarding one or more non-radioactive stains with thermal neutrons thereby forming said radioactive stain composition.

11. The process of claim 10, wherein the non-radioactive stain bombarded by thermal neutrons contains sulfur, thereby rendering the sulfur radioactive after bombardment.

12. The process of claim 11, wherein said non-radioactive stain is selected from the group consisting of Coomassie Blue, Ponceau, Light Green, Fast Green, Amido Black or a mixture thereof.

13. A radioactive stain composition produced by bombarding one or more non-radioactive stain compositions with thermal neutrons, thereby rendering said non-radioactive stain compositions radioactive, wherein said non-radioactive stain composition is selected from the group consisting of Coomassie Blue, Ponceau, Light Green, Fast Green, Amido Black or a mixture thereof.

14. A method of identifying proteins with a radioactive stain composition, comprising the steps of:
   (a) placing the protein in a gel;
   (b) forming a radioactive stain composition; and
   (c) applying the radioactive stain composition to the gel;
   thereby allowing identification of the protein in the gel.

15. The method of claim 14, wherein step (b) comprises bombarding a non-radioactive stain with thermal neutrons, thereby rendering the stain radioactive.

16. The method of claim 14, wherein step (b) comprises combining radioactive iron isotope and ferrous bathophenanthroline sulfonate.

17. A protein or plurality of proteins stained with one or more radioactive stain compositions produced by:
   (a) placing the protein or proteins in a gel;
   (b) forming a radioactive stain composition; and
   (c) applying said radioactive stain composition to said gel; thereby causing coordination of said radioactive stain composition with said protein or proteins.

* * * * *

UNITED STATES PATENT AND TRADEMARK OFFICE
CERTIFICATE OF CORRECTION

PATENT NO. : 4,459,356
DATED : JULY 10, 1984
INVENTOR(S) : DOUGLAS GERSTEN, EDWARD ZAPOLSKI, ROBERT LEDLEY

It is certified that error appears in the above-identified patent and that said Letters Patent is hereby corrected as shown below:

Cover Page, under "OTHER PUBLICATIONS", right-hand column,
line 6, change "$Fe^{2-}$" to --$Fe^{2+}$--;
line 7, delete "+";
line 10, change "Analys" to --Analysis--;

Column 2, line 11, change "compensation" to --composition--;
lines 60-68, the descriptions of the two figures are reversed; therefore, the description which is now for figure 1 should be substituted with that which is now for figure 2 and vice versa.

Column 3, line 22, change "excission" to --excision--;
line 67, change "(SCF)" to --(FCF)--;

Column 4, line 25, change "FIG. 1" to --FIG. 2--;
line 32, change "FIG. 2" to --FIG. 1--.

Signed and Sealed this

Ninth Day of April 1985

[SEAL]

Attest:

DONALD J. QUIGG

Attesting Officer   Acting Commissioner of Patents and Trademarks